United States Patent [19]

Storni

[11] Patent Number: 4,489,069
[45] Date of Patent: Dec. 18, 1984

[54] SUBSTITUTED THIAZOLIDINYL ESTERS OF MINERAL ACIDS

[75] Inventor: Angelo Storni, Rheinfelden, Switzerland

[73] Assignee: Ciba-Geigy AG, Basel, Switzerland

[21] Appl. No.: 434,304

[22] Filed: Oct. 14, 1982

[30] Foreign Application Priority Data

Jan. 22, 1982 [CH] Switzerland ............................ 406/82

[51] Int. Cl.³ ................. C07D 417/12; A61K 31/425
[52] U.S. Cl. ..................................... 424/202; 424/270; 548/117; 548/183
[58] Field of Search ................ 548/183, 117; 424/270, 424/202

[56] References Cited

U.S. PATENT DOCUMENTS 3,699,116 10/1972 Meisels et al. .................... 260/306.7

FOREIGN PATENT DOCUMENTS 1455512 11/1976 United Kingdom .

Primary Examiner—Robert Gerstl
Attorney, Agent, or Firm—Michael W. Glynn

[57] ABSTRACT

Compounds of the formula

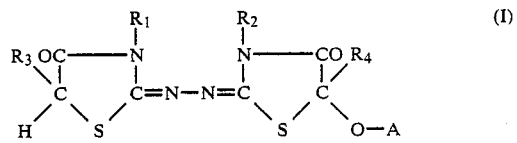

in which one of the symbols $R_1$ and $R_2$ represents an alkyl radical that has 3 or 4 carbon atoms and is unsaturated in the 2,3-position, and the other represents such a radical or lower alkyl, $R_3$ and $R_4$ each represents, independently of the other, hydrogen or methyl, and A represents a radical of the formula

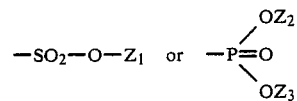

(Ia)   (Ib)

in which $Z_1$, or each of $Z_2$ and $Z_3$ independently of the other, represents hydrogen or lower alkyl, or $Z_2$ and $Z_3$ together represent lower alkylene, and salts of such compounds in which $Z_1$, or $Z_3$ and optionally also $Z_2$, represent(s) hydrogen, exhibit tumor-inhibiting activities.

22 Claims, No Drawings

SUBSTITUTED THIAZOLIDINYL ESTERS OF MINERAL ACIDS

The invention relates to novel substituted thiazolidinyl esters of mineral acids and to salts of such compounds having valuable pharmacological properties, to processes for the manufacture of these novel substances, to pharmaceutical preparations that contain these substances and to the use of these substances and preparations containing them.

The compounds according to the invention correspond to the general formula

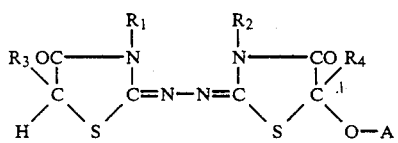

in which one of the symbols $R_1$ and $R_2$ represents an alkyl radical that has 3 or 4 carbon atoms and is unsaturated in the 2,3-position, and the other represents such a radical or lower alkyl, $R_3$ and $R_4$ each represents, independently of the other, hydrogen or methyl, and A represents a radical of the formula

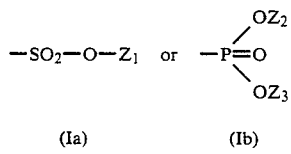

in which $Z_1$, or each of $Z_2$ and $Z_3$, independently of the other, represents hydrogen or lower alkyl, or $Z_2$ and $Z_3$ together represent lower alkylene. The invention relates also to salts of compounds of the general formula I in which $Z_1$, or $Z_3$ and optionally also $Z_2$, represent(s) hydrogen, with bases, especially to the pharmaceutically acceptable salts with bases.

In the compounds of the general formula I, an alkyl radical $R_1$ and/or $R_2$ that is unsaturated in the 2,3-position contains a double or triple bond and is, for example, allyl, 1- or 2-methallyl or 2-propynyl. A lower alkyl radical $R_1$ or $R_2$, and lower alkyl which may be present as $Z_1$ or as $Z_2$ and $Z_3$, contains up to 7, preferably up to 4, carbon atoms and is, for example, pentyl, isopentyl, neopentyl, hexyl or heptyl, or preferably propyl, isopropyl, butyl or isobutyl, but especially ethyl or, more especially, methyl. Lower alkylene formed by $Z_2$ and $Z_3$ together has from 2 to 5 carbon atoms with 3 or, preferably, 2 chain members and is, for example, propylene, 1,2-dimethylethylene, trimethylene, 2-methyltrimethylene, 1,3- or 2,2-dimethyltrimethylene or, especially, ethylene.

Salts with bases of compounds of the general formula I that are capable of salt formation are, for example, metal salts, such as alkali metal salts, for example sodium or potassium salts, or alkaline earth metal salts, such as magnesium or calcium salts, and also ammonium salts and salts with primary, secondary or tertiary monoacidic or polyacidic organic bases, such as, for example, ethylamine, 2-aminoethanol, diethylamine, iminodiethanol, triethylamine, 2-(diethylamino)-ethanol, nitrilotriethanol or pyridine, or 1,2-ethanediamine. The corresponding pharmaceutically acceptable, non-toxic salts are preferred.

Compounds of the general formula I having a radical A of the partial formula Ib can, according to the definitions of $Z_2$ and $Z_3$, be in the form of either neutral phosphoric acid esters or acidic, that is to say monobasic (with $Z_2$ as lower alkyl and $Z_3$ as hydrogen) or dibasic (with $Z_2$ and $Z_3$ as hydrogen), phosphoric acid esters.

The compounds of the formula I can be in the form of isomeric mixtures, for example mixtures of racemates (diastereoisomeric mixture) or racemates, or in the form of pure isomers, for example pure racemates or optical antipodes.

The novel compounds of the general formula I and the salts of such compounds exhibit valuable pharmacological properties, especially tumour-inhibiting activity. This can be demonstrated in tests on animals, for example by the oral or parenteral, such as intraperitoneal or subcutaneous, administration of doses of between 10 and 250 mg/kg in Ehrlich carcinoma in mice transplant: $1 \times 10^6$ cells (Ascites) i.p. to female mice NMRI), in Walker carcinosarcoma 256 in rats (transplant: 0.5 ml of a suspension of solid tumours in Hanks solution s.c. or i.m. to male rats (Wistar)), in transplantable mammary adenocarcinoma R 3230 AC in rats (transplant: 0.5 ml of a suspension of solid tumours in Hanks solution s.c. or i.m. to female rats (Fischer)) and especially in mammary carcinoma in rats induced by 7,12-dimethylbenz[α]anthracene (DMBA) (induced by the p.o. administration of 15 mg of DMBA in 1 ml of sesame oil to 50 day old female rats (Sprague Dawley), it being possible to detect multiple tumours after 6 to 8 weeks).

Thus, for example, in Ehrlich carcinoma, after intraperitoneal administration 4 times (4 hours after, and then 1, 2 and 3 days after transplantation: 10 animals per dose; the quantity of Ascites in ml is determined 10 days after transplantation); in Walker carcinosarcoma 256, after oral or intraperitoneal administration four times (1, 2, 3 and 4 days after transplantation; 8 to 10 animals per dose; the tumour weight in grams is determined 10 days after transplantation), and in mammary adenocarcinoma R 3230 AC, after oral or intraperitoneal administration 10 times (5 times per week for two weeks commencing 4 hours after transplantation; 10 to 15 animals per dose; the tumour weight in grams is determined 20 days after transplantation), it is possible to detect the following inhibition of tumour growth in comparison with untreated control animals:

| Compound (Example) | Ehrlich Ascites carcinoma dose (mg/kg) | Inhibition of tumour growth (in %) | Walker carcinosarcoma 256 dose (mg/kg) | Inhibition of tumour growth (in %) | mammary adenocarcinoma R 3230 Ac dose (mg/kg) | Inhibition of tumour growth (in %) |
|---|---|---|---|---|---|---|
| 1 | 4 × 50 i.p. | 94 | 4 × 50 i.p. | 84 | 10 × 50 i.p. | 62 |
|   |             |    | 4 × 250 p.o. | 53 | 10 × 250 p.o. | 43 |
| 5 | 4 × 50 i.p. | 42 | 4 × 50 p.o. | 72 | — | — |

| | Ehrlich Ascites carcinoma | | Walker carcinosarcoma 256 | | mammary adenocarcinoma R 3230 Ac | |
|---|---|---|---|---|---|---|
| Compound (Example) | dose (mg/kg) | Inhibition of tumour growth (in %) | dose (mg/kg) | Inhibition of tumour growth (in %) | dose (mg/kg) | Inhibition of tumour growth (in %) |
| 6 | 4 × 100 i.p. | 70 | 4 × 100 i.p. | 53 | — | — |
| 7 | 4 × 100 i.p. | 51 | 4 × 50 i.p. | 31 | — | — |
| | | | 4 × 250 p.o. | 32 | | |
| 10 | 4 × 50 i.p. | 21 | — | | — | — |
| 11 | 4 × 50 i.p. | 49 | — | | — | — |

(Method of administration: i.p.: intraperitoneal, and p.o.: oral)

In the case of DMBA-induced mammary carcinoma, the following inhibition of tumour growth and of the re-formation of tumours can be detected after treatment for 5 weeks (25 individual doses) and 6 weeks (30 individual doses); (the figures given show the average size of all tumours in all the test animals):

| Compound (Example) | dose mg/kg | average tumour size (treated/ untreated test animals) [a] | tumour reduction (in percent) |
|---|---|---|---|
| 1 | 30 × 10 s.c. | 1.13/24.73 | 95 |
| | 30 × 25 p.o. | 2.50/20.63 | 88 |
| 5 | 25 × 25 i.p. | 6.31/15.97 | 61 |
| | 25 × 100 p.o. | 0.96/19.03 | 95 |
| 6 | 25 × 100 p.o. | 2.13/21.55 | 90 |
| 7 | 30 × 10 s.c. | 2.27/24.82 | 91 |
| | 30 × 25 p.o. | 6.38/21.04 | 70 |
| 10 | 30 × 10 s.c. | 8.77/22.27 | 61 |
| | 30 × 25 p.o. | 6.07/22.27 | 72 |
| 11 | 30 × 10 s.c. | 9.03/22.27 | 59 |
| | 30 × 25 p.o. | 5.65/22.27 | 75 |

Method of administration:
S.C.: subcutaneous;
p.o.: oral;
i.p.: intraperitoneal;
[a] the figures given show the average size of all tumors in all the test animals.

In comparison with the strong tumour-inhibiting activity, the toxicity and side-effects of the compounds according to the invention are low to moderate (maximum single dose tolerated: intraperitoneal administration: between 500 and 1250 mg/kg; and oral administration: more than 2500 mg/kg), so that they can be used as such or, especially, in the form of pharmaceutical preparations for the treatment of neoplastic diseases in warm-blooded animals by enteral, especially oral, or parenteral administration of therapeutically effective doses, and especially for the treatment of mammary carcinoma.

The invention relates especially to those compounds of the general formula I in which one of the radicals $R_1$ and $R_2$ represents allyl or 2-methallyl, and the other also represents one of these groups or, preferably, methyl, whilst $R_3$, $R_4$ and A can have the meanings given under formula I but A is especially a radical of the partial formula Ia in which $Z_1$ represents hydrogen, or, preferably, is a radical of the partial formula Ib in which $Z_2$ represents lower alkyl, especially methyl, and $Z_3$ represents lower alkyl, especially methyl, or hydrogen, and salts, especially pharmaceutically acceptable salts with bases, of such compounds in which $Z_1$, or $Z_3$ and optionally $Z_2$, represent(s) hydrogen, for example the corresponding alkali metal salts, such as the sodium salts.

The invention relates more especially to compounds of the formula I in which $R_1$ represents allyl or 2-methallyl, and $R_2$ also represents one of these radicals or, preferably, methyl, $R_3$ represents hydrogen or, especially, methyl, and $R_4$ represents hydrogen, whilst A has the meaning given under formula I but has especially the preferred meanings indicated above, and in the radical of the formula Ib $Z_2$ is especially methyl or hydrogen, and $Z_3$ is especially methyl or hydrogen, and salts, especially pharmaceutically acceptable salts, of such compounds in which $Z_1$, or $Z_3$ and optionally $Z_2$, represent(s) hydrogen.

The invention relates most especially to the compounds and salts, preferably pharmaceutically acceptable salts, for example alkali metal salts, of corresponding salt-forming compounds, described in the Examples, and more especially 3-methyl-2-[[5-methyl-3-(2-methallyl)-4-oxo-5-thiazolidinylidene]-hydrazono]-4-oxo-5-thia-zolidinyl hydrogen sulphate and methyl-3-methyl-2-[[5-methyl-3-(2-methallyl)-4-oxo-2-thiazolidinylidene]-hydrazono]-4-oxo-2-thiazolidinyl hydrogen phosphate, and especially their salts, such as pharmaceutically acceptable salts, such as, for example, the corresponding alkali metal salts, such as the sodium salts.

The novel compounds of the general formula I can be manufactured according to processes known per se. Thus they can be manufactured by (a) reacting a compound of the formula

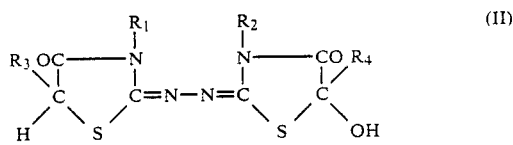

with a compound that introduces the radical of the partial formula Ia or Ib, or (b) in a compound of the formula

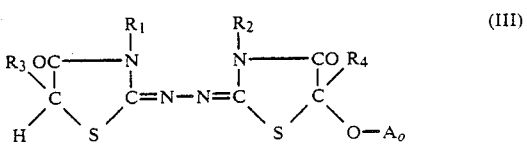

in which $A_o$ represents a radical of the formula

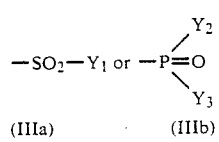

in which $Y_1$ or $Y_3$ represents a radical that can be replaced by the group $O$-$Z_1$ or $O$-$Z_3$, respectively, or by a salt form thereof, and $Y_2$ represents a radical $O$-$Z_2$ or a radical that can be replaced by the group $O$-$Z_2$ or by a salt form thereof, replacing the radical $Y_1$ or the radical $Y_3$ by the group $O$-$Z_1$ or $O$-$Z_3$, respectively, or by a salt form thereof, and optionally replacing the radical $Y_2$ by the group $O$-$Z_2$ or by a salt form thereof, and, if desired, converting a compound of the general formula I into a different compound of the general formula I, and/or, if desired, converting a salt obtainable according to the process into the free compound or into a different salt, and/or converting a compound of the formula I obtainable according to the process in which $Z_1$, or $Z_3$ and optionally $Z_2$, represent(s) hydrogen into a salt thereof, and/or, if desired, separating an isomeric mixture obtainable according to the process into the isomers.

Compounds that introduce a radical of the formula Ia or Ib are, for example, sulphur trioxide, which may also be used in the form of complexes, such as the pyridine complex, or compounds of the general formulae

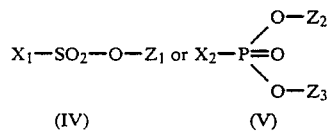

in which $X_1$ or $X_2$ represents reactive functionally modified hydroxy. The latter is, for example, especially hydroxy esterified by an inorganic or organic acid, such as hydroxy esterified by a hydrohalic acid or an aryl- or alkane-sulphonic acid, for example p-toluenesulphonic acid or methane- or ethane-sulphonic acid. $X_1$ or $X_2$ is especially halogen, such as bromine and, especially, chlorine. As starting materials of the formula IV there come into consideration, for example, chlorosulphonic acid and the lower alkyl esters thereof, and as starting materials of the formula V, for example, di-lower alkyl- or lower alkylene-phosphorochloridates or alternatively corresponding phosphorobromidates.

It is preferable to carry out the reaction with sulphur trioxide in an inert solvent or solvent mixture, the reaction with the sulphur trioxide/pyridine complex being carried out, for example, in methylene chloride or dimethylformamide or mixtures thereof with pyridine, and reactions with sulphur trioxide being carried out, for example, in dimethylformamide. The reaction temperatures are between approximately 0° and approximately 100° C.; the operation is preferably carried out at room temperature or at slightly elevated temperature. When using the sulphur trioxide/pyridine complex there is obtained as a direct reaction product a pyridinium salt of compounds of the formula I which may be converted into the corresponding acids or, preferably, directly into other salts, such as, for example, alkali metal salts. When using sulphur trioxide, free acids are produced which, if desired, can be converted directly, that is to say without prior working up, into salts, for example alkali metal salts.

The reaction of compounds of the formula II with those of the formula IV or V is preferably carried out in an inert, especially aprotic organic solvent, such as, for example, methylene chloride, acetonitrile, dimethylformamide or dimethyl sulphoxide, and preferably in the presence of an acid-binding agent, such as an organic base, for example tri-lower alkylamine, such as ethyldiisopropylamine or triethylamine, and also, for example, pyridine, or imidazole, or an alkali metal-lower alkoxide, for example sodium methoxide or ethoxide, or an inorganic base, for example sodium or potassium hydroxide, and in the presence of a basic ion exchanger. The reaction temperature selected is, for example, between 0° and approximately 100° C., preferably room temperature or slightly elevated temperature, and, if necessary, the reaction can be carried out in a closed vessel and/or under an inert gas atmosphere, such as a nitrogen atmosphere.

The starting materials of the formula II are known (for example German Offenlegungsschrift No. 2 405 395) or can be manufactured analogously to the compounds described therein).

In the starting materials of the formula III, radicals $Y_1$, or $Y_3$ and optionally $Y_2$, are, for example, esterified hydroxy groups, such as hydroxy groups esterified by strong acids, for example by mineral acids, and also by strong organic acids, or etherified hydroxy groups, for example hydroxy groups etherified by aliphatic, cycloaliphatic, aromatic or araliphatic radicals, such as corresponding optionally substituted hydrocarbon radicals. Esterified hydroxy groups are especially halogen, such as chlorine or bromine, whilst etherified hydroxy groups are, inter alia, aryloxy, such as phenoxy or p-nitrophenoxy, or aryl-lower alkoxy, such as, especially, benzyloxy, and also p-nitrobenzyloxy, and lower alkenyloxy, for example allyloxy, and also lower alkoxy, such as, for example, the groups $-OZ_1$, $-OZ_2$ and $-OZ_3$.

Compounds of the general formula I in which $Z_1$, or $Z_3$ and optionally $Z_2$, represent(s) hydrogen can be obtained by hydrolysis, such as by the action of water, optionally in the form of mixtures with suitable organic solvents, such as dioxan or lower alkanols, on compounds of the general formula III in which the radicals $Y_1$, or $Y_3$ and optionally $Y_2$, represent esterified hydroxy groups, such as halogen. Such compounds of the formula I can be produced from starting materials of the formula III in which $Y_1$, $Y_2$ and/or $Y_3$ represent suitably esterified hydroxy groups also in the absence of water, for example by transesterification, such as in the case of the action with a suitable alcohol, for example α-methylbenzyl alcohol. The same end products can be obtained, by basic hydrolysis, both from the afore-mentioned starting materials of the general formula III and from those in which $Y_1$, or $Y_3$ and optionally $Y_2$, represent aryloxy or aralkoxy groups, for example by the action of bases in the presence of at least equimolar amounts of water, preferably in water-containing organic solvents, such as corresponding lower alkanols or dioxan. As bases there may be used either organic, preferably tertiary, bases, such as those mentioned hereinbefore, or inorganic bases, such as sodium or potassium hydroxide, it being possible to obtain the reaction products either directly in the form of salts or, after treatment with an acidic reagent, in the form of free acids.

In starting materials of the formula III in which $Y_1$, and especially $Y_3$ and optionally $Y_2$, represent(s) etherified hydroxy, especially lower alkoxy and more especially methoxy, such a radical may advantageously be replaced by hydroxy by means of a nucleophilic substitution reaction; in this operation, in a corresponding starting material in which the two radicals $Y_2$ and $Y_3$ represent etherified hydroxy, for example methoxy, if desired only one of the etherified hydroxy groups can be cleaved. The cleaving can be effected by treatment of the corresponding starting material of the formula III with a suitable nucleophilic reagent, such a reagent preferably containing a hydroxy or, especially, mercapto group capable of being etherified or an amino group capable of being substituted, including quaternised. Such reagents are, inter alia, an optionally substituted thiophenolate compound, such as thiophenol in the presence of an inorganic or organic base, such as triethylamine, or a suitable urea, or, especially, thiourea compound, such as thiourea, and also a suitable, preferably sterically hindered, amine compound, such as a corresponding lower alkylamine, for example tert.-butylamine and also tri-lower alkylamine, such as trimethylamine, N-lower alkyl-morpholine or -thiomorpholine, for example N-methylmorpholine, or pyridine.

The cleaving of an etherified hydroxy group $Y_1$, or $Y_3$ and optionally $Y_2$, can be effected also by treatment with a strong inorganic base, such as an alkali metal hydroxide, for example sodium or potassium hydroxide, preferably in the presence of an alcohol, such as a lower alkanol, for example ethanol, or ammonium hydroxide, or with a suitable neutral salt, especially an alkali metal or alkaline earth metal halide or thiocyanate, such as sodium iodide, barium iodide or sodium thiocyanate, this method being suitable especially for cleaving lower alkenyloxy groups, for example allyloxy groups, or aryl-lower alkoxy groups, for example benzyloxy groups.

Furthermore, suitably etherified hydroxy groups $Y_1$, or $Y_3$ and optionally $Y_2$, especially aromatically or araliphatically etherified hydroxy groups, such as optionally substituted phenoxy or benzyloxy, can be cleaved by hydrogenolysis, such as by treatment with hydrogen in the presence of a noble metal catalyst, such as a platinum or palladium catalyst, it being necessary to take care that a lower alkenyl group $R_1$ or $R_2$ is not also reduced.

Furthermore, in starting materials of the formula III, esterified hydroxy groups $Y_1$, or $Y_3$ and optionally $Y_2$, such as halogen, can be replaced by lower alkoxy by reacting a corresponding compound with a lower alkanol in the presence of a base under substantially anhydrous reaction conditions, or with a lower alkoxide of an alkali, alkaline earth or earth metal, such as a sodium or potassium methoxide, ethoxide or tert.-butoxide.

The above reactions are carried out in a manner known per se in the absence or, preferably, in the presence of a suitable inert solvent, such as an optionally halogenated hydrocarbon, for example benzene or methylene chloride, a lower alkanol, for example methanol, dimethyl sulphoxide or acetonitrile, or a solvent mixture, and customarily under mild reaction conditions, preferably at temperatures of between approximately $-10°$ C. and approximately $100°$ C., especially at room temperature or slightly elevated temperatures up to approximately $50°$ C., if necessary in a closed vessel and/or under an inert gas atmosphere, such as a nitrogen atmosphere. The reaction products can be separated off in the form of free acids or can be converted directly into the salts, for example alkali metal salts.

Starting materials of the formula III in which $Y_1$, or $Y_3$ and optionally $Y_2$, represent(s) an etherified hydroxy group, such as lower alkoxy, aryloxy or aryl-lower alkoxy, can be manufactured in accordance with process (a).

It is also possible to obtain analogously to process (a) starting materials of the formula III in which $Y_1$, or $Y_3$ and optionally $Y_2$, represent(s) esterified hydroxy, especially halogen, such as chlorine, by reacting a compound of the formula II under mild reaction conditions, for example, with an equimolar amount of sulphuryl chloride or phosphorus oxychloride. The compounds of the formula III obtainable in this manner are preferably further reacted directly, in accordance with process (b), for example by treatment with water or a water-containing organic solvent, to form compounds of the formula I in which $Z_1$, or $Z_3$ and $Z_2$, represent(s) hydrogen, or salts thereof, or, for example, by treatment with alkali metal-lower alkoxides, such as sodium methoxide or ethoxide, to form compounds of the formula I in which $Z_1$, or $Z_3$ and optionally $Z_2$, represent(s) lower alkyl.

Compounds of the formula I obtainable according to the invention can be converted into different compounds of the formula I in a manner known per se. Thus, in accordance with the above process modification (b), compounds of the formula I in which A has the partial formula Ia or, especially, Ib, and $Z_1$ or $Z_2$ represents lower alkyl and $Z_3$ represents hydrogen or lower alkyl, a lower alkyl group $Z_1$ or $Z_2$ representing especially methyl, can be converted into compounds of the formula I in which the radical A has the partial formula Ia or Ib in which $Z_1$ or $Z_2$ represents hydrogen and $Z_3$ represents hydrogen or lower alkyl.

Furthermore, in compounds of the formula I having the partial formulae Ia and Ib in which $Z_1$, $Z_2$ and/or $Z_3$ represent hydrogen, these groups can be replaced by lower alkyl, for example by treatment of the corresponding compound or a salt thereof with a reactive ester of a lower alkanol and a strong acid, such as a corresponding lower alkylhalide, for example a chloride, bromide or iodide, or a corresponding arene- or lower alkane-sulphonic acid lower alkyl ester, for example p-toluenesulphonic acid lower alkyl ester or methane-sulphonic acid lower alkyl ester.

Salts of salt-forming compounds of the formula I obtainable according to the invention can be converted into the free compounds in a manner known per se, for example by treatment with an acidic reagent, such as an acid, or into different salts by salt interchange.

Salts of compounds of the formula I that are suitable for salt formation, especially pharmaceutically acceptable salts, such as, for example, those mentioned above, can be manufactured in a manner known per se, for example by treatment with a suitable base, such as an alkali metal hydroxide, ammonia or a salt-forming amine.

Mixtures of isomers can be separated into the pure isomers in a manner known per se, racemic mixtures inter alia by means of physical separation, for example fractional crystallisation or distillation, or chromatography, inter alia high pressure liquid chromatography, and racemates inter alia with the formation of salts with optically active bases and separation of the resulting salt mixtures, for example by fractional crystallisation.

The invention relates also to those embodiments of the process in which a starting material is formed under the reaction conditions, or in which a reactant is optionally in the form of its salts.

The starting materials used for carrying out the reactions according to the invention are advantageously those which result in the groups of end products given special mention at the beginning and especially in the end products specifically described or pointed out.

The present invention relates also to the use of the novel compounds as pharmacologically active, especially as carcinostatically active, compounds. The daily doses of such compounds are, for mammals, depending upon species, age, individual condition, and on the method of administration, between approximately 2 mg and approximately 250 mg, especially between approximately 5 mg and approximately 100 mg, per kg body weight, and within this range the doses in the case of parenteral administration, for example intramuscular or subcutaneous injection, or intravenous infusion, are generally lower than in the case of enteral, that is to say oral or rectal, administration. The compounds of the formula I and pharmaceutically acceptable salts of such compounds having salt-forming properties are used orally or rectally preferably in dosage unit forms, such as tablets, dragées or capsules or suppositories, and parenterally especially in the form of injectable solutions, emulsions or suspensions or in the form of infusion solutions, there coming into consideration as solutions especially solutions of salts.

The invention relates also to pharmaceutical preparations for enteral, for example oral or rectal, or parenteral administration, which contain a therapeutically effective amount of a compound of the formula I or a pharmaceutically acceptable salt of such a compound having salt-forming properties, optionally together with a pharmaceutically acceptable carrier or carrier mixture, it being possible for these carriers to be inorganic or organic, and solid or liquid. Corresponding dosage unit forms, especially for peroral use, for example dragées, tablets or capsules, preferably contain from approximately 50 mg to approximately 500 mg, especially from approximately 100 mg to approximately 400 mg, of a compound of the formula I or a pharmaceutically acceptable salt of a corresponding compound that is capable of salt formation together with pharmaceutically acceptable carriers.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores can be provided with suitable coatings that are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain substances which increase the viscosity, for example sodium carboxymethylcellulose, sorbitol and/or dextran, and, optionally, stabilisers.

The pharmaceutical preparations of the present invention can be manufactured in a manner known per se, for example by means of conventional mixing, granulating, confectioning, dissolving and lyophilising processes. Thus pharmaceutical preparations for oral use can be obtained by mixing the active ingredient with solid carriers, optionally granulating a resulting mixture and, if desired or necessary after the addition of suitable adjuncts, processing the mixture or granulate to form tablets or dragée cores.

The following Examples illustrate the invention described above but do not restrict the scope of the invention in any way. Temperatures are given in degrees Centigrade.

EXAMPLE 1

56 g (0.35 mol) of sulphur trioxide/pyridine complex are added to a solution of 32.8 g (0.1 mol) of 5-hydroxy-3-methyl-2-[[5-methyl-3-(2-metallyl)-4-oxo-2-thiazolidinylidene]-hydrazono]-4-thiazolidinone in 700 ml of methylene chloride and 200 ml of anhydrous pyridine and the mixture is stirred at 20°-25° for 20 hours. Then 700 ml of water are added and the mixture is stirred for a further 20 minutes and the two layers are separated. The methylene chloride solution is dried over magnesium sulphate and concentrated by evaporation in a water-jet vacuum. 500 ml of diethyl ether are added to the residue and the yellow reaction product that precipitates out is filtered with suction and washed three times with acetone and then with diethyl ether. The resulting pyridinium [3-methyl-2-[[5-methyl-3-(2-metallyl)-4-oxo-5-thiazolidinylidene]-hydrazono]-4-oxo-5-thiazolidinyl]-sulphate melts at 187°.

For conversion into the sodium salt, 48.7 g (0.10 mol) of the above pyridinium salt are dissolved in 1100 ml of methylene chloride and 100 ml of methanol and, while stirring well, a sodium methoxide solution, prepared from 2.3 g (0.10 mol) of sodium and 50 ml of methanol, is added dropwise thereto and the desired sodium salt precipitates out. After the addition of 300 ml of ether the salt is filtered with suction and washed twice with methylene chloride, once with diethyl ether/methanol 4:1 and then with ether. After drying in a high vacuum at 60°, the resulting sodium [3-methyl-2-[[5-methyl-3-(2-methallyl)-4-oxo-2-thiazolidinylidene]-hydroazono]-4-oxo-5-thiazolidinyl]-sulphate melts at 195° (with decomposition).

EXAMPLE 2

In a manner analogous to that described in Example 1, using as starting materials 31.4 g (0.10 mol) of 5-hydroxy-2-[(3-methyl-4-oxo-2-thiazolidinylidene)hydrazono]-3-(2-methallyl)-4-thiazolidinone and 56 g (0.35 mol) of sulphur trioxide/pyridine complex there is obtained pyridinium [2-[(3-methyl-4-oxo-2-thiazolidinylidene)-hydrazono]-3-(2-methallyl)-4-oxo-5-thiazolidinyl]-sulphate having a melting point of 161°–168°; and also in a manner analogous to that described in Example 1, the corresponding sodium salt, having a melting point of 216° (with decomposition), is obtained from 47.4 g (0.10 mol) of the pyridinium salt in 800 ml of methylene chloride and a sodium methoxide solution of 2.3 g (0.10 mol) of sodium and 200 ml of methanol.

EXAMPLE 3

To a solution of 31.4 g (0.1 mol) of 5-hydroxy-2-[(3-methyl-4-oxo-2-thiazolidinylidene)-hydrazono]-3-(2-methallyl)-4-thiazolidinone in 500 ml of methylene chloride and 100 ml of pyridine there is added a suspension that has been prepared beforehand from a solution of 23.3 g (0.34 mol) of chlorosulphonic acid in 400 ml of methylene chloride by the dropwise addition of 180 ml of pyridine at a reaction temperature of from −10° to 0° under a nitrogen atmosphere. The resulting reaction mixture is stirred at 20°–25° for 20 hours. Then 700 ml of water are added and the mixture is stirred for a further 20 minutes and the two layers are separated. The methylene chloride solution is dried over magnesium sulphate and then concentrated by evaporation in a water-jet vacuum. The resulting pyridinium [2-[(3-methyl-4-oxo-2-thiazolidinylidene)-hydrazono]-3-(2-methallyl)-4-oxo-5-thiazolidinyl]-sulphate melts at 190°–191°.

For conversion into the sodium salt, 47.3 g (0.10 mol) of the above pyridinium salt are dissolved in 600 ml of methylene chloride and 400 ml of dimethylformamide and, while stirring well, a 2.95% strength sodium methoxide solution in methanol is added dropwise thereto. The sodium salt is precipitated out by the addition of 1500 ml of diethyl ether; the salt is filtered with suction, washed once with a 4:1 mixture of diethyl ether and methanol and then with diethyl ether. After drying under a high vacuum at 60°, the sodium 2-[(3-methyl-4-oxo-2-thiazolidinylidene)-hydrazono]-3-(2-methallyl)-4-oxo-5-thiazolidinyl]-sulphate melts at 216° (with decomposition).

EXAMPLE 4

In a manner analogous to that described in Example 3, using as starting materials 60.1 g (0.20 mol) of 3-allyl-5-hydroxy-2-[(3-methyl-4-oxo-2-thiazolidinylidene)-hydrazono]-4-thiazolidinone, 46.6 ml (0.70 mol) of chlorosulphonic acid and 250 ml of pyridine in 700 ml of methylene chloride and, for conversion into the sodium salt, 100 ml of a 3.4% strength sodium methoxide solution in methanol, there is obtained sodium [3-allyl-2-[(3-methyl-4-oxo-2-thiazolidinylidene)-hydrazono]-4-oxo-5-thiazolidinyl]-sulphate having a melting point of 217° (decomposition).

EXAMPLE 5

In a manner analogous to that described in Example 1, using as starting materials 68 g (0.20 mol) of 3-allyl-2-[(3-allyl-5-methyl-4-oxo-2-thiazolidinylidene)-hydrazono]-5-hydroxy-4-thiazolidinone, 81.6 g (0.7 mol) of chlorosulphonic acid, 300 ml of pyridine in 400 ml of methylene chloride and, for conversion into the sodium salt, 50 ml of a 7.6% strength sodium methoxide solution in methanol, there is obtained sodium [3-allyl-2-[(3-allyl-5-methyl-4-oxo-2-thiazolidinylidene)-hydrazono]-4-oxo-5-thiazolidinyl]-sulphate having a melting point of 190° (decomposition).

EXAMPLE 6

While stirring, 21 ml (0.2 mol) of dimethyl phosphorochloridate are added dropwise to a solution of 33 g (0.10 mol) of 5-hydroxy-3-methyl-2-[[5-methyl-3-(2-methallyl)-4-oxo-2-thiazolidinylidene]-hydrazono]-4-thiazolidinone and 43 ml of ethyldiisopropylamine in 250 ml of methylene chloride. The reaction is at first slightly exothermic and the reaction temperature is maintained at 25° by cooling. After the addition is complete, the reaction mixture is stirred at room temperature for a further 2 hours. The mixture is then extracted by shaking firstly with 100 ml of ice-cold 2N hydrochloric acid and then with two 100 ml portions of water. The methylene chloride solution is dried over magnesium sulphate and concentrated by evaporation in a water-jet vacuum. Dimethyl-[3-methyl-2-[[5-methyl-3-(2-methallyl)-4-oxo-2-thiazolidinylidene]-hydrazono]-4-oxo-5-thiazolidinyl]-phosphate remains behind as the residue and, after recrystallising once from diethyl ether, melts at 99°–103°.

EXAMPLE 7

While stirring, 56 ml of triethylamine are added dropwise to a solution of 22 g (0.05 mol) of dimethyl-[3-methyl-2-[[5-methyl-3-(2-methallyl)-4-oxo-2-thiazolidinylidene]-hydrazono]-4-oxo-5-thiazolidinyl]-phosphate and 26 ml of thiophenol in 70 ml of dioxan, the reaction temperature rising to 40°. The reaction mixture is then stirred at room temperature for a further two hours. Then 400 ml of diethyl ether are added and a heavy oil separates out.

The ether solution is decanted off and the oil that remains is dissolved in 200 ml of isopropanol and, while stirring, a sodium methoxide solution, prepared from 1.15 g (0.05 mol) of sodium and 30 ml of methanol, is added thereto. Sodium methyl-[3-methyl-2-[[5-methyl-3-(2-methallyl)-4-oxo-2-thiazolidinylidene]-hydrazono]-4-oxo-5-thiazolidinyl]-phosphate separates out. This is filtered with suction, washed with a small quantity of isopropanol and diethyl ether and then dried in a high vacuum at 60° for 15 hours. Melting point 146°–150°.

This product is a diastereoisomeric mixture which can be separated into the two racemates, for example by means of high pressure liquid chromatography using a stationary phase of silica gel with a chemically bonded C 18 phase (for example Hibar LiChroCart HPLC cartridge, filled with LiChrosorb RP 18, column composition: 250×4 mm, by Merck AG, Darmstadt, Federal Republic of Germany) and a liquid phase, for example a 40:40:20 mixture of methanol/water/0.01 molar aqueous sodium dihydrogenphosphate.

EXAMPLE 8

While stirring at 5°-10°, 16.7 ml (0.12 mol) of triethylamine are added dropwise to a suspension of 30 g (0.10 mol) of 2-[(3-allyl-4-oxo-2-thiazolidinylidene)-hydrazono]-5-hydroxy-3-methyl-4-thiazolidinone and 21.7 g (0.15 mol) of dimethyl phosphorochloridate in 250 ml of methylene chloride. The reaction is slightly exothermic and the suspended substances, with the exception of the triethylamine hydrochloride that is formed, enter into solution. When the addition is complete, the reaction mixture is stirred at room temperature for a further one hour. The mixture is then extracted by shaking firstly with 200 ml of ice-cold water and then with 100 ml of ice-cold saturated sodium bicarbonate solution. The methylene chloride solution is dried over magnesium sulphate and concentrated under reduced pressure until crystallisation begins. 100 ml of diethyl ether are added to the residue and the [2-[(3-allyl-4-oxo-2-thiazolidinylidene)-hydrazono]-3-methyl-4-oxo-5-thiazolidinyl]-dimethyl phosphate is filtered with suction. Melting point 147°-148°.

The starting material may be prepared as follows:

(a) While stirring, 17.1 g (0.10 mol) of 3-allyl-2,4-thiazolidinedione-2-hydrazone [colourless oil, cf. U.S. Pat. No. 3,699,116, Example 8(a) to (d)] and 8.0 g (0.11 mol) of methyl isothiocyanate are boiled under reflux in 70 ml of isopropanol for 2 hours, and 3-allyl-2,4-thiazolidinedione-2-(4-methyl-3-thiosemicarbazone) separates out in the form of a coarse, crystalline precipitate. This is cooled with ice, filtered with suction and washed with a 1:1 mixture of pentane and diethyl ether. Melting point: 148°-151°.

(b) 11.0 g (0.12 mol) of glyoxylic acid monohydrate are dissolved in 40 ml of dioxan and the solution is then diluted with 200 ml of carbon tetrachloride. Then, while stirring, 24.4 g (0.10 mol) of 3-allyl-2,4-thiazolidinedione-2-(4-methyl-3-thiosemicarbazone) are introduced. The mixture is then heated and, with the simultaneous dropwise addition of 120 ml of carbon tetrachloride, 120 ml of an azeotropic mixture of carbon tetrachloride and water are distilled off in a descending condenser. The mixture is cooled to 20°, and the crystal mass is diluted with 100 ml of diethyl ether; the crystals are filtered with suction and then washed with diethyl ether. The resulting 2-[(3-allyl-4-oxo-2-thiazolidinylidene)-hydrazono]-5-hydroxy-3-methyl-4-thiazolidinone melts at 209°-210°.

EXAMPLE 9

In a manner analogous to that described in Example 8, using as starting materials 31.4 g (0.10 mol) of 2-[(3-allyl-5-methyl-4-oxo-2-thiazolidinylidene)-hydrazono]-5-hydroxy-3-methyl-4-thiazolidinone, 21.7 g (0.15 mol) of dimethyl phosphorochloridate and 16.7 ml (0.12 mol) of triethylamine in 250 ml of methylene chloride there is obtained [2-[(3-allyl-5-methyl-4-oxo-2-thiazolidinylidene)-hydrazono]-3-methyl-4-oxo-5-thiazolidinyl]-dimethyl phosphate having a melting point of 102°-107°.

The starting material is prepared as follows:

(a) 11.0 g (0.12 mol) of glyoxylic acid monohydrate are dissolved in 40 ml of dioxan and the solution is then diluted with 200 ml of carbon tetrachloride. Then, while stirring, 25.8 g (0.10 mol) of 3-allyl-5-methyl-2,4-thiazolidinedione-2-(4-methyl-3-thiosemicarbazone) [cf. U.S. Pat. No. 3,699,116, Example 8(a) to (e)] are introduced. The reaction mixture is then heated and, with the simultaneous dropwise addition of 120 ml of carbon tetrachloride, 120 ml of an azeotropic mixture of carbon tetrachloride and water are distilled off in a descending condenser. The mixture is cooled to 20° and the crystal mass is diluted with 100 ml of diethyl ether and 200 ml of pentane; the crystals are filtered with suction and washed with a 2:1 mixture of pentane and diethyl ether. The resulting 2-[(3-allyl-5-methyl-4-oxo-2-thiazolidinylidene)-hydrazono]-5-hydroxy-3-methyl-4-thiazolidinone melts at 164°-166°.

EXAMPLE 10

While stirring, 41.4 ml (0.30 mol) of triethylamine are added dropwise to a suspension of 40.8 g (0.10 mol) of 2-[(3-allyl-4-oxo-2-thiazolidinylidene)-hydrazono]-3-methyl-4-oxo-5-thiazolidinyl]-dimethyl phosphate and 20.5 ml (0.20 mol) of thiophenol in 250 ml of isopropanol and the reaction temperature rises to 30°. The clear yellow reaction solution is then stirred at 35° for a further 4 hours. Then, at 30°-35°, a sodium methoxide solution prepared from 2.3 g (0.10 mol) of sodium and 50 ml of methanol is added dropwise thereto. Sodium [2-[(3-allyl-4-oxo-2-thiazolidinylidene)-hydrazono]-3-methyl-4-oxo-5-thiazolidinyl]-methyl phosphate separates out. This is filtered with suction and washed with isopropanol and diethyl ether. After recrystallisation from a 4:1 mixture of isopropanol and water, the product melts at 200°-205° (with decomposition).

EXAMPLE 11

In a manner analogous to that described in Example 10, using as starting materials 42.2 g (0.10 mol) of [2-[(3-allyl-5-methyl-4-oxo-2-thiazolidinylidene)-hydrazono]-3-methyl-4-oxo-5-thiazolidinyl]-dimethyl phosphate, 20.5 ml (0.20 mol) of thiophenol and 41.4 ml (0.30 mol) of triethylamine in 250 ml of isopropanol and, for conversion into the sodium salt, treating the product with 23 ml of a 10% strength (w/v) methanolic sodium methoxide solution, there is obtained sodium [2-[(3-allyl-5-methyl-4-oxo-2-thiazolidinylidene)-hydrazono]-3-methyl-4-oxo-5-thiazolidinyl]-methyl phosphate having a melting point of 190° (decomposition).

EXAMPLE 12

While stirring and cooling at 4°, a solution of 0.4 g of tert.-butylamine in 5 ml of methylene chloride is added dropwise over a period of 7 minutes to a mixture of 2.18 g of dimethyl-[3-methyl-2-[[5-methyl-3-(2-methallyl)-4-oxo-2-thiazolidinylidene]-hydrazono]-4-oxo-5-thiazolidinyl]-phosphate and 12 ml of methylene chloride under a nitrogen atmosphere. The temperature of the clear yellow solution is allowed to rise to room temperature; the solution is stirred for 3½ hours and 1 ml of tert.-butylamine is added. Stirring is carried out for a further 16 hours at room temperature, a further 2 ml of tert.-butylamine are then added to the reaction mixture and stirring is continued for a further 29½ hours. The mixture is diluted with 20 ml of diethyl ether and the precipitate is filtered off and washed with a 1:3 mixture of methylene chloride and diethyl ether and then with diethyl ether, yielding (N-methyl-tert.-butylammonium) methyl-[3-methyl-2-[[5-methyl-3-(2-methallyl)-4-oxo-2-thiazolidinylidene]-hydrazono]-4-oxo-5-thiazolidinyl]-phosphate which melts at 216°-217° (with decomposition) and which is dried at room temperature under a high vacuum for 15 hours. It can be converted into the sodium salt, for example by treatment with a methanolic sodium methoxide solution.

EXAMPLE 13

While stirring, a mixture of 2.2 g of dimethyl-[3-methyl-2-[[5-methyl-3-(2-methallyl)-4-oxo-2-thiazolidinylidene]-hydrazono]-4-oxo-5-thiazolidinyl]-phosphate and 0.38 g of thiourea in 2.5 ml of methanol are boiled under reflux at a bath temperature of 70°–80° for 6 hours and a solution is produced which is left to stand for 16 hours and which then solidifies to form a crystal mass. This is diluted with 4 to 5 ml of diethyl ether, and the solid material is crushed, filtered off and washed with a 2:1 mixture of diethyl ether and methanol and then with diethyl ether. The resulting (S-methylisothiuronium) methyl-[2-methyl-2-[[5-methyl-3-(2-methallyl)-4-oxo-2-thiazolidinylidene]-hydrazono]-4-oxo-5-thiazolidinyl]-phosphate melts at 189°–191° (with decomposition) and can be converted into the sodium salt, for example by treatment with a methanolic sodium methoxide solution.

EXAMPLE 14

While stirring, 120 ml of 1N hydrochloric acid are added to a solution of 49.4 g of sodium methyl-[3-methyl-2-[[5-methyl-3-(2-methallyl)-4-oxo-2-thiadiazolidinylidene]-hydrazono]-4-oxo-5-thiazolidinyl]-phosphate in 800 ml of water (deionised). A thick semi-gelatinous mass is produced which is dissolved in 1500 ml of dioxan at 30°–35°. The solution is diluted with 2500 ml of methylene chloride; the mixture is shaken and the layers are allowed to separate. The aqueous phase is separated off and extracted twice using 200 ml of methylene chloride each time. The combined organic solutions are washed once with 400 ml of a 1:1 mixture of a concentrated aqueous sodium chloride solution and with water and dried over 200 g of magnesium sulphate for 5 minutes. The mixture is filtered, washed with a 1:2 mixture of dioxan and methylene chloride and the filtrate is concentrated by evaporation under reduced pressure at a bath temperature of 45°–50° to a volume of 800 ml and a crystalline precipitate is formed which is filtered off and washed twice with a small quantity of dioxan and then with diethyl ether. There is thus obtained methyl-[3-methyl-2-[[5-methyl-3-(2-methallyl)-4-oxo-2-thiazolidinylidene]-hydrazono]-4-oxo-5-thiazolidinyl]-hydrogen phosphate which melts at 193°–194°.

EXAMPLE 15

While stirring, a suspension of 7 g of methyl-[3-methyl-2-[[5-methyl-3-(2-methallyl)-4-oxo-2-thiazolidinylidene]-hydrazono]-4-oxo-5-thiazolidinyl]-hydrogen phosphate (Example 14) in 40 ml of distilled water is adjusted to pH 7 by the addition of approximately 4% strength aqueous potassium hydroxide and the slightly turbid solution is treated with approximately 0.5 g of activated carbon and filtered. The filtrate is concentrated under reduced pressure to a weight of approximately 15 g and the syrup-like residue, which contains some solid substance, is dissolved in 50 ml of isopropanol and, while stirring, diethyl ether is added in portions. A viscous precipitate is produced; a relatively large amount of diethyl ether is added and the supernatant solution is decanted off; approximately 40 ml of acetone are added to the residue, producing a powder-like precipitate. Diethyl ether is again added but the precipitate is not filtered and is drained into another vessel with the aid of acetone; 20 ml of isopropanol are added and the whole is diluted with 150 ml of diethyl ether, yielding potassium methyl-[3-methyl-2-[[5-methyl-3-(2-methallyl)-4-oxo-2-thiazolidinylidene]-hydrazono]-4-oxo-5-thiazolidinyl]-phosphate, which can now be filtered, and which is dried under reduced pressure at 60° for 24 hours. Melting point 167°–170° (decomposition from 177°).

EXAMPLE 16

While stirring, a suspension of 8 g of methyl-(3-methyl-2-[[5-methyl-3-(2-methallyl)-4-oxo-2-thiazolidinylidene]-hydrazono]-4-oxo-2-thiazolidinyl]-hydrogen phosphate (Example 14) in 50 ml of distilled water is adjusted to pH 7–8 with an approximately 4% strength aqueous ammonium hydroxide solution. The slightly turbid solution is cleared with activated carbon and filtered and the filtrate is concentrated under reduced pressure to a weight of 20 g. This is diluted with 80 ml of isopropanol, and diethyl ether is added until the mixture begins to become turbid. Crystallisation can be initiated by inoculation. The ammonium methyl-[3-methyl-2-[[5-methyl-3-(2-methallyl)-4-oxo-2-thiazolidinylidene]-hydrazono]-4-oxo-5-thiazolidinyl]-phosphate is filtered off and dried in a high vacuum at room temperature for 20 hours. Melting point: 195°–197°.

EXAMPLE 17

While stirring, a 5% aqueous solution of 2-hydroxyethylamine is added, in portions, to a suspension of 1 g of methyl-[3-methyl-2-[[5-methyl-2-(2-methallyl)-4-oxo-2-thiazolidinylidene]-hydrazono]-4-oxo-5-thiazolidinyl]-hydrogen phosphate (Example 14) in 10 ml of distilled water until a pH value of 7–8 has been reached. The solution is cleared with 0.3 g of activated carbon, filtered and concentrated under reduced pressure to a weight of approximately 2 g. The semi-solid residue is taken up in 7 ml of absolute ethanol, and diethyl ether is added until the mixture begins to become turbid. The precipitate so obtained is dissolved in approximately 20 ml of methanol, a small quantity of activated carbon is added to the solution and the whole is filtered; the now clear filtrate is concentrated to a volume of approximately 5 ml. The (2-hydroxyethylammonium) methyl-[3-methyl-2-[[5-methyl-3-(2-methallyl)-4-oxo-2-thiazolidinylidene]-hydrazono]-4-oxo-5-thiazolidinyl]-phosphate is caused to crystallise by the addition of diethyl ether and then filtered off. Melting point: 186°–187°.

EXAMPLE 18

A suspension of 1 g of methyl-[3-methyl-2-[[5-methyl-3-(2-methallyl)-4-oxo-2-thiazolidinylidene]-hydrazono]-4-oxo-5-thiazolidinyl]-hydrogen phosphate (Example 14) in 10 ml of distilled water is adjusted to pH 7–8 by the addition in portions, while stirring, of a 5% aqueous solution of tri-(2-hydroxyethyl)-amine. A clear solution is obtained which becomes turbid after about 5 minutes and is concentrated under reduced pressure to a weight of 3 g. The mixture is diluted with 20 ml of absolute ethanol, stirred with 0.5 g of activated carbon and filtered. The now clear filtrate is concentrated under reduced pressure to a weight of approximately 3 g, the [tri-(2-hydroxyethyl)-ammonium]methyl-[3-methyl-2-[[5-methyl-3-(2-methallyl)-4-oxo-2-thiazolidinylidene]-hydrazono]-4-oxo-5-thiazolidinyl]-phosphate beginning to crystallise. 10 ml of absolute ethanol and, in portions, 10 ml of diethyl ether are added, the salt is filtered off and dried under a high vacuum at 40° for 6 hours. Melting point: 145°–146°.

EXAMPLE 19

Coated tablets containing 300 mg of sodium [3-methyl-2-[[5-methyl-3-(2-methallyl)-4-oxo-2-thiazolidinylidene]-hydrazono]-4-oxo-5-thiazolidinyl]-sulphate can be manufactured as follows:

| Composition for 10,000 tablets | |
|---|---|
| sodium [3-methyl-2-[[5-methyl-3-(2-methylallyl)-4-oxo-2-thiazolidinylidene]-hydrazono]-4-oxo-5-thiazolidinyl]-sulphate | 3000.0 g |
| maize starch | 680.0 g |
| colloidal silica | 200.0 g |
| magnesium stearate | 20.0 g |
| stearic acid | 50.0 g |
| sodium carboxymethyl starch | 250.0 g |
| water | q.s. |

A mixture of the sodium [3-methyl-2-[[5-methyl-3-(2-methallyl)-4-oxo-2-thiazolidinylidene]-hydrazono]-4-oxo-5-thiazolidinyl]-sulphate, 50 g of maize starch and the colloidal silica is worked into a moist mass with a starch paste of 250 g of maize starch and 2.2 kg of demineralised water. This is forced through a sieve of 3 mm mesh width and dried at 45° in a fluidised bed drier for 30 minutes. The dry granulate is pressed through a sieve of 1 mm mesh width, mixed with a previously sieved mixture (1 mm sieve) of 330 g of maize starch, the magnesium stearate, the stearic acid and the sodium carboxymethyl starch and pressed into slightly curved tablets.

The tablet compacts are coated in a confectioning boiler of 45 cm diameter by uniform spraying for 30 minutes with a solution of 20 g of shellac and 40 g of hydroxypropylmethylcellulose (low viscosity) in 110 g of methanol and 1350 g of methylene chloride; drying is carried out by simultaneously blowing in air at 60°.

Instead of the above-mentioned active ingredient it is also possible to use the same amount of a different active ingredient from the preceding Examples, such as sodium [3-allyl-2-[(3-methyl-4-oxo-2-thiazolidinylidene)-hydrazono]-4-oxo-5-thiazolidinyl]-sulphate, dimethyl-[3-methyl-2-[[5-methyl-3-(2-methallyl)-4-oxo-2-thiazolidinylidene]-hydrazono]-4-oxo-5-thiazolidinyl]-phosphate, sodium methyl-[3-methyl-2-[[5-methyl-3-(2-methallyl)-2-thiazolidinylidene]-hydrazono]-4-oxo-5-thiazolidinyl]-phosphate, or (2-hydroxyethylammonium) methyl-[3-methyl-2-[[5-methyl-3-(2-methallyl)-2-thiazolidinylidene]-hydrazono]-4-oxo-5-thiazolidinyl]-phosphate.

EXAMPLE 20

Hard gelatine capsules are filled with, in each case, 300 mg of sodium 3-methyl-2-[[5-methyl-3-(2-methallyl)-4-oxo-2-thiazolidinylidene]-hydrazono]-4-oxo-5-thiazolidinyl]-sulphate, mixed with 60 mg of rice starch.

Instead of the above active ingredient it is also possible to use the same quantity of sodium or (2-hydroxymethylammonium) methyl-[3-methyl-2-[[5-methyl-3-(2-methallyl)-4-oxo-2-thiazolidinylidene]-hydrazono]-4-oxo-5-thiazolidinyl]-phosphate.

EXAMPLE 21

Ampoules are filled with, in each case, 5 ml of a sterile 4% strength aqueous solution of sodium [3-methyl-2-[[5-methyl-3-(2-methallyl)-4-oxo-2-thiazolidinylidene]-hydrazono]-4-oxo-5-thiazolidinyl]-sulphate corresponding to 200 mg of active ingredient, and the ampoules are sealed and examined.

Instead of the above active ingredient it is also possible to use the same quantity of sodium or (2-hydroxyethylammonium) methyl-[3-methyl-2-[[5-methyl-3-(2-methallyl)-4-oxo-2-thiazolidinylidene]-hydrazono]-4-oxo-5-thiazolidinyl]-phosphate.

We claim:

1. A compound of the general formula

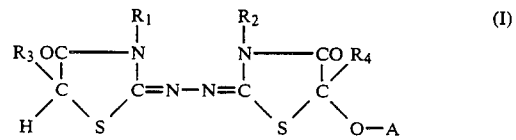

in which one of the symbols $R_1$ and $R_2$ represents an alkyl radical that has 3 or 4 carbon atoms and is unsaturated in the 2,3-position, and the other represents such a radical or lower alkyl, $R_3$ and $R_4$ each represents, independently of the other, hydrogen or methyl, and A represents a radical of the formula

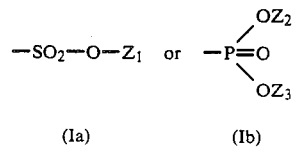

(Ia)      (Ib)

in which $Z_1$, or each of $Z_2$ and $Z_3$ independently of the other, represents hydrogen or lower alkyl, or $Z_2$ and $Z_3$ together represent lower alkylene, and salts of such compounds in which $Z_1$, or $Z_3$ and optionally also $Z_2$, represent(s) hydrogen.

2. A compound as claimed in claim 1 in which one of the symbols $R_1$ and $R_2$ represents allyl, 1-methallyl, 2-methallyl or 2-propynyl, and the other also represents one of these groups or methyl, and $R_3$, $R_4$ and A have the meanings given in claim 1, and salts of such compounds in which $Z_1$, or $Z_3$ and optionally also $Z_2$, represent(s) hydrogen.

3. A compound as claimed in claim 1 in which one of the radicals $R_1$ and $R_2$ represents allyl or 2-methallyl, and the other also represents one of these groups or methyl, and $R_3$, $R_4$ and A have the meanings given in claim 1, and salts of such compounds in which $Z_1$, or $Z_3$ and optionally also $Z_2$, represent(s) hydrogen.

4. A compound as claimed in claim 1 in which one of the radicals $R_1$ and $R_2$ represents allyl or 2-metallyl, and the other also represents one of these groups or methyl, $R_3$ and $R_4$ have the meanings given in claim 1, and A represents a radical of the partial formula Ia in which $Z_1$ represents hydrogen, or represents a radical of the partial formula Ib in which $Z_2$ represents lower alkyl and $Z_3$ represents lower alkyl or hydrogen, and salts of such compounds in which $Z_1$, or $Z_3$ and optionally also $Z_2$, represent(s) hydrogen.

5. A compound as claimed in claim 1 in which $R_1$ represents allyl or 2-methallyl and $R_2$ also represents one of these radicals or methyl, $R_3$ represents hydrogen or methyl, $R_4$ represents hydrogen, and A represents a radical of the partial formula Ia in which $Z_1$ represents hydrogen, or represents a radical of the partial formula Ib in which $Z_2$ represents methyl and $Z_3$ represents hydrogen or methyl, and salts of such compounds in which $Z_1$, or $Z_3$ and optionally also $Z_2$, represent(s) hydrogen.

6. A compound as claimed in claim 1 and being [3-methyl-2-[[5-methyl-3-(2-methallyl)-4-oxo-2-thiazolidinylidene]-hydrazono]-4-oxo-5-thiazolidinyl]-hydrogen sulphate and salts thereof.

7. A compound as claimed in claim 1 and being [2-[(3-methyl-4-oxo-2-thiazolidinylidene)-hydrazono]-3-(2-methallyl)-4-oxo-5-thiazolidinyl]-hydrogen sulphate and salts thereof.

8. A compound as claimed in claim 1 and being [3-allyl-2-[(3-methyl-4-oxo-2-thiazolidinylidene)-hydrazono]-4-oxo-5-thiazolidinyl]-hydrogen sulphate and salts thereof.

9. A compound as claimed in claim 1 and being [3-allyl-2-[(3-allyl-5-methyl-4-oxo-2-thiazolidinylidene)-hydrazono]-4-oxo-5-thiazolidinyl]-hydrogen sulphate and salts thereof.

10. A compound as claimed in claim 1 and being dimethyl-[3-methyl-2-[[5-methyl-3-(2-methallyl)-4-oxo-2-thiazolidinylidene]-hydrazono]-4-oxo-5-thiazolidinyl]-phosphate.

11. A compound as claimed in claim 1 and being methyl-[3-methyl-2-[[5-methyl-3-(2-methallyl)-4-oxo-2-thiazolidinylidene]-hydrazono]-4-oxo-2-thiazolidinyl]-hydrogen phosphate and salts thereof.

12. A compound as claimed in claim 1 and being sodium methyl-[3-methyl-2-[[5-methyl-3-(2-methallyl)-4-oxo-2-thiazolidinylidene]-hydrazono]-4-oxo-2-thiazolidinyl]-hydrogen phosphate.

13. A compound as claimed in claim 1 and being (2-hydroxyethylammonium)-methyl-[3-methyl-2-[[5-methyl-3-(2-methallyl)-4-oxo-2-thiazolidinylidene]-hydrazono]-4-oxo-2-thiazolidinyl]-hydrogen phosphate.

14. A compound as claimed in claim 1 and being [2-[(3-allyl-4-oxo-2-thiazolidinylidene)-hydrazono]-3-methyl-4-oxo-5-thiazolidinyl]-dimethyl phosphate.

15. A compound as claimed in claim 1 and being [2-[(3-allyl-5-methyl-4-oxo-2-thiazolidinylidene)-hydrazono]-3-methyl-4-oxo-5-thiazolidinyl]-dimethyl phosphate.

16. A compound as claimed in claim 1 and being [2-[(3-allyl-4-oxo-2-thiazolidinylidene)-hydrazono]-3-methyl-4-oxo-5-thiazolidinyl]-methylhydrogen phosphate and salts thereof.

17. A compound as claimed in claim 1 and being methyl-[2-[(3-allyl-5-methyl-4-oxo-2-thiazolidinylidene)-hydrazono]-3-methyl-4-oxo-5-thiazolidinyl]-hydrogen phosphate and salts thereof.

18. A pharmaceutical composition containing an antineoplastic therapeutically effective amount of a compound according to claim 1, together with a pharmaceutically acceptable carrier.

19. A pharmaceutical composition according to claim 18, containing methyl-[3-methyl-2-[[5-methyl-3-(2-methallyl)-4-oxo-2-thiazolidinylidene]-hydrazono]-4-oxo-2-thiazolidinyl]-hydrogen phosphate or a salt thereof.

20. A pharmaceutical composition according to claim 19, containing sodium methyl-[3-methyl-2-[[5-methyl-3-(2-methylallyl)-4-oxo-2-thiazolidinylidene]-hydrazono]-4-oxo-2-thiazolidinyl]-hydrogen phosphate.

21. A pharmaceutical composition according to claim 19, containing (2-hydroxyethylammonium)-methyl-[3-methyl-2-[[5-methyl-3-(2-methallyl)-4-oxo-2-thiazolidinylidene]-hydrazono]-4-oxo-2-thiazolidinyl]-hydrogen phosphate.

22. A method of treatment of neoplastic diseases in a mammal, comprising the administration of a therapeutically effective amount of a compound of the formula I according to claim 1 or of a salt thereof to the mammal in need of the same.

* * * * *

UNITED STATES PATENT AND TRADEMARK OFFICE
CERTIFICATE OF CORRECTION

PATENT NO. : 4,489,069
DATED : December 18, 1984
INVENTOR(S) : Angelo Storni

It is certified that error appears in the above-identified patent and that said Letters Patent is hereby corrected as shown below:

Claim 20, Column 20, Line 27 should read--

(2-methallyl)-4-oxo-2-thiazolidinylidene]-hydrazono]- --.

Signed and Sealed this

Eighth Day of October 1985

[SEAL]

Attest:

DONALD J. QUIGG

Attesting Officer

Commissioner of Patents and Trademarks—Designate